United States Patent
Axelgaard

(10) Patent No.: US 7,695,430 B2
(45) Date of Patent: Apr. 13, 2010

(54) REVERSE CURRENT CONTROLLING ELECTRODE WITH OVERSIZE BACKING

(75) Inventor: Jens Axelgaard, Fallbrook, CA (US)

(73) Assignee: Axelgaard Manufacturing Company, Ltd., Fallbrook, CA (US)

( * ) Notice: Subject to any disclaimer, the term of this patent is extended or adjusted under 35 U.S.C. 154(b) by 883 days.

(21) Appl. No.: 11/335,990

(22) Filed: Jan. 20, 2006

(65) Prior Publication Data
US 2006/0116565 A1    Jun. 1, 2006

Related U.S. Application Data

(63) Continuation-in-part of application No. 10/359,988, filed on Feb. 6, 2003, now Pat. No. 7,324,847.

(51) Int. Cl.
*A61N 1/04* (2006.01)
(52) U.S. Cl. ....................................... 600/142
(58) Field of Classification Search ................. 600/382, 600/384, 393; 607/142
See application file for complete search history.

(56) References Cited

U.S. PATENT DOCUMENTS

| | | | |
|---|---|---|---|
| 4,522,211 A * | 6/1985 | Bare et al. ................... | 600/392 |
| 4,708,149 A | 11/1987 | Axelgaard et al. | |
| 4,722,354 A | 2/1988 | Axelgaard et al. | |
| 4,736,752 A | 4/1988 | Munck et al. | |
| 5,038,796 A | 8/1991 | Axelgaard et al. | |
| 5,904,712 A | 5/1999 | Axelgaard | |
| 6,038,464 A | 3/2000 | Axelgaard et al. | |
| 6,600,957 B2 * | 7/2003 | Gadsby ...................... | 607/142 |
| 6,687,524 B1 | 2/2004 | Svejk | |
| 6,795,722 B2 | 9/2004 | Sheraton et al. | |
| 6,950,688 B2 | 9/2005 | Axelgaard et al. | |

* cited by examiner

*Primary Examiner*—Carl H Layno
*Assistant Examiner*—Frances P Oropeza
(74) *Attorney, Agent, or Firm*—Walter A. Hackler

(57) ABSTRACT

A medical electrode includes a moderately conductive flexible member having a top side and a bottom side with a connector and contact with a flexible member top side for establishing electrical contact with an external apparatus. An oversize non-conductive flexible sheet covers the conductive flexible member top and the connector and a highly conductive ink pattern is disposed on a conductive flexible member bottom side. A moderately high conductive hydrogel adhesive disposed on the conductive flexible member bottom side and covering the conductive ink pattern is provided for adhering the electrode to a patient's skin.

6 Claims, 5 Drawing Sheets

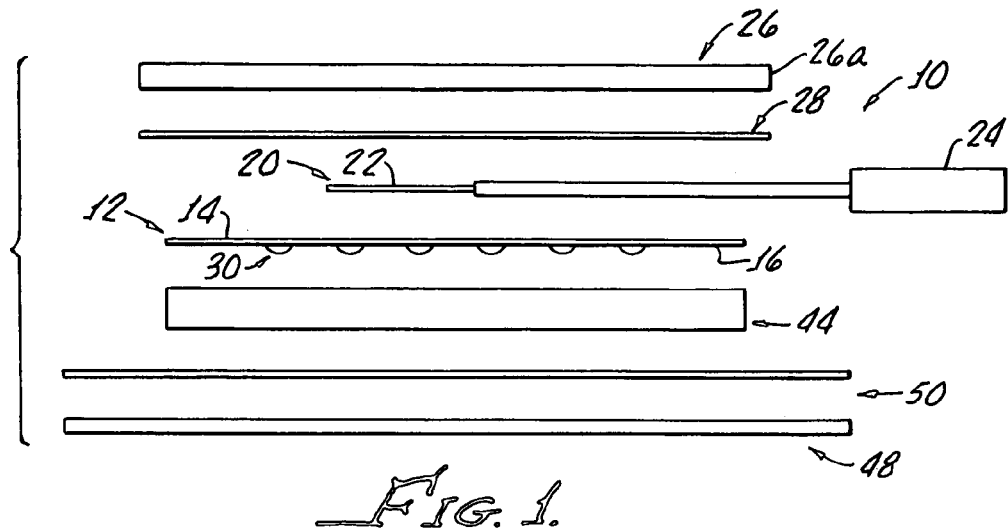
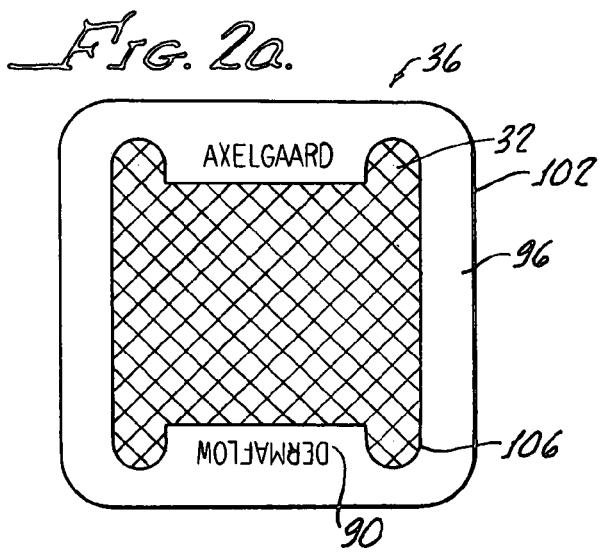
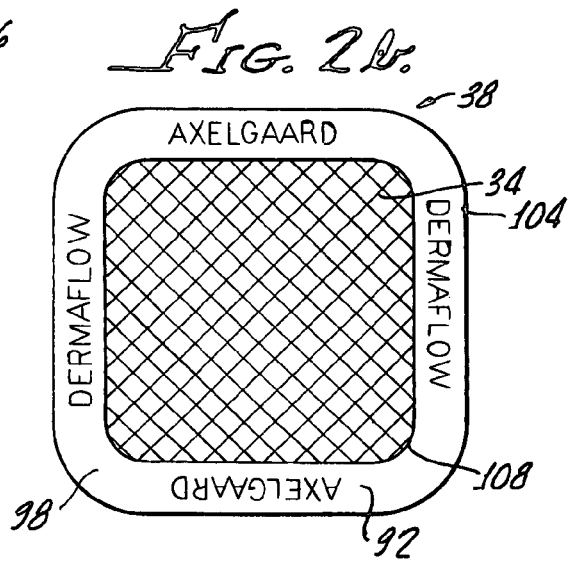

REVERSE CURRENT CONTROLLING ELECTRODE WITH OVERSIZE BACKING

The present application is a continuation-in-part of U.S. Ser. No. 10/359,988 filed Feb. 6, 2003 now U.S. Pat. No. 7,324,847. This reference patent application is to be incorporated herein in toto by the specific reference thereto.

The present invention generally relates to electrodes and, more particularly, electrodes suitable for transcutaneous nerve and/or muscle stimulation and biological signal recording.

Medical electrodes must provide an even electrical distribution to a patient's skin over an entire surface of the electrode to assure proper coupling. Because of the curvaceous nature of the human body, it is apparent that medical electrodes for use thereon must be flexible not only for confirmation with a patient's skin contours, but also to accommodate relative movement of the patient's skin.

It is well known that inadequate flexing and shaping of the electrode to a patient's contour can result in an irritation of the patient's skin. Electrical "hot spots" due to uneven electrode-skin contact can result in a rash or a burning sensation. A sensation of burning may be felt by a patient within a few minutes after application of the electrical signals during nerve and/or muscle stimulation, while rash conditions generally take a longer period of time to develop.

In order to provide uniform electrical coupling, heretofore developed electrodes have utilized conductive fabrics and foils in combination with a conductive and flexible adhesive in order to uniformly couple electrical signals to and/or from an electrical lead wire, or connector. A number of electrodes have provided impedance compensation for directing electrical pulses from the lead wire uniformly throughout an electrode, such as, for example, U.S. Pat. No. 5,038,796 entitled, ELECTRICAL STIMULATION ELECTRODE WITH IMPEDANCE COMPENSATION, and U.S. Pat. No. 5,904,712 CURRENT CONTROLLING ELECTRODE to Axelgaard. U.S. Pat. No. 4,736,752 teaches the control of current density across an electrode through the use of conductive ink design areas. These patents are incorporated in their entirety herewith by this specific reference thereto.

Many prior art electrodes have compromised the flexibility of the electrode in order to provide adequate current densities over the entire contact area of the electrode. Such electrodes typically have utilized a metallic mesh, or foil, to provide conductivity and utilize a conductive gel between the electrode and the patient's skin in order to accommodate the movement therebetween. Such use of foil or mesh often cause burning or hot spots at electrode edges.

The present invention is directed to a medical electrode having a combination of conductive elements, with selected conductivities which enables assembly of the electrode in a manner hereinbefore not possible. More specifically, the present invention is directed to a medical electrode having a connector disposed on a top surface of a conductive member. This enables automated assembly of the electrode as opposed to conventional manual assembly which in turn reduces unit cost while at the same time providing for controlled and even current density.

SUMMARY OF THE INVENTION

A medical electrode in accordance with the present invention generally includes a moderately conductive flexible member having a top side and a bottom side with a highly conductive pattern, such as, for example conductive ink, printed or transferred to the member bottom side.

A conductive adhesive of moderately high conductivity is disposed on the flexible member bottom side and covering the conductive pattern for adhering the electrode to a patients' skin.

Importantly, the use of a moderately high conductivity adhesive enables the placement of a connector on the top side of the flexible member while at the same time providing uniform current distribution by the electrode. This arrangement is reverse to the configuration of prior art electrode such as set forth in U.S. Pat. No. 5,904,712 and accordingly has been named "Reverse Current Controlling Electrode".

In controlling current density, the surface resistivity of the conductive member may be between about $10^2$ and about $10^6$ ohm/cm, the resistivity of the conductive pattern may be between about 0.1 and about 10 ohm and the volume resistivity of the adhesive may be between about $10^2$ and $10^4$ ohm cm. The conductivity of the conductive pattern can be controlled through the use of various grid designs with preselected line widths and spacing as well as thickness and ink compositions.

The connector is disposed over the conductive ink pattern and on the top side of the conductive member, whereas the ink pattern is disposed on the bottom side of the conductive member. This arrangement enables the connectors to be disposed in any selected points within a perimeter of the pattern without affecting current distribution. This flexibility of connector positioning, provided by the present invention, facilitates manufacture of the electrodes. In addition, because the lead wire is not disposed between the conductive pattern and patients' skin, there is no interference with the electrode current distribution as is the case when the lead wire is disposed between the conductive pattern and the patients' skin as is the case with some prior art electrodes.

A non-conductive flexible sheet may be disposed over the connector on the conductive flexible member top side. The non-conductive flexible sheet preferably has dimensions greater than said conductive flexible member causing an overlap thereof. This arrangement facilitates manufacture and also eliminates the need for precise alignment with the conductive flexible member. It also prevents gel from folding around an edge of the conductive flexible member and attaching itself to clothing, etc.

An adhesive is provided for bonding the non-conductive flexible sheet to the top side of said conductive flexible member and also for securing said connector to said conductive flexible member top side;

In one embodiment of the present invention, the conductive pattern is disposed on the conductive flexible member bottom at a spaced apart distance from a perimeter of the conductive flexible member in order to establish a border between the perimeter of the conductive ink pattern and the conductive flexible member perimeter. This is important in providing controlled "roll off" of electrical current distribution. While even and uniform electrical current density across the electrode is the desired distribution, such current density should not be present at the edge of the electrode since it may cause unwanted stimulation at that site. Thus, it is most desirable to have the current density "roll off" or be reduced to zero over a short distance. The border arrangement in accordance with the present invention provides for such desired current roll off while providing uniform current distribution over the electrode from border to border.

In addition, the present invention provides for indicia, which is printed on the conductive flexible member in the border region and not contacting the conductive ink pattern, for conveying written information to a user. The indicia when disposed in the border do not affect current distribution or current "roll off" at electrode edges. Visual observation of the indicia is enhanced through the utilization of a conductive hydrogel adhesive with sufficient transparency to enable the user to read the indicia therethrough.

In yet another embodiment of the present invention, the medical electrode includes a moderately conductive flexible member having a top and a bottom side with a plurality of connectors in contact with the conductive member top side for establishing electrical contact with external apparatus, and a plurality of highly conductive patterns are disposed on the conductive flexible member bottom side where each electrode is electrically isolated from an adjacent electrode.

This feature provides for the advantage of fixed electrode distances which assures proper application of the electrode for optimum patient stimulation or signal recording when multiple electrodes are utilized.

A moderately high conductive adhesive is disposed on the conductive member bottom side and covers the conductive ink patterns for adhering the electrode to a patient's skin.

It should be appreciated that the lead wire may be attached or held in place on the conductive flexible member top side in any manner, and inasmuch as the current distribution across the electrode conductive gel is controlled by the relative conductivities of the flexible member, ink pattern and the adhesive, the connector can be placed anywhere within the borders of the ink pattern as hereinabove noted.

BRIEF DESCRIPTION OF THE DRAWINGS

The present invention may be better understood with reference to the following detailed description, taken in conjunction with the accompanying drawings, in which:

FIG. 1 is an exploded cross-sectional view of a medical electrode in accordance with the present invention generally showing a moderately conductive flexible member having a top side and a bottom side, a connector in contact with the member top side, and a non-conductive flexible sheet covering the moderately conductive flexible member top side and the connector, the sheet having dimensions greater than the flexible member; a highly conductive pattern is disposed on the member bottom side, along with a moderately high conductive adhesive and a plastic carrier with a release layer, the carrier preventing premature and/or inadvertent contact with the hydrogel;

FIGS. 2a and 2b are plan views of two embodiments of the present invention showing different ink patterns and indicia for identifying the electrodes;

DETAILED DESCRIPTION

Figure 3:
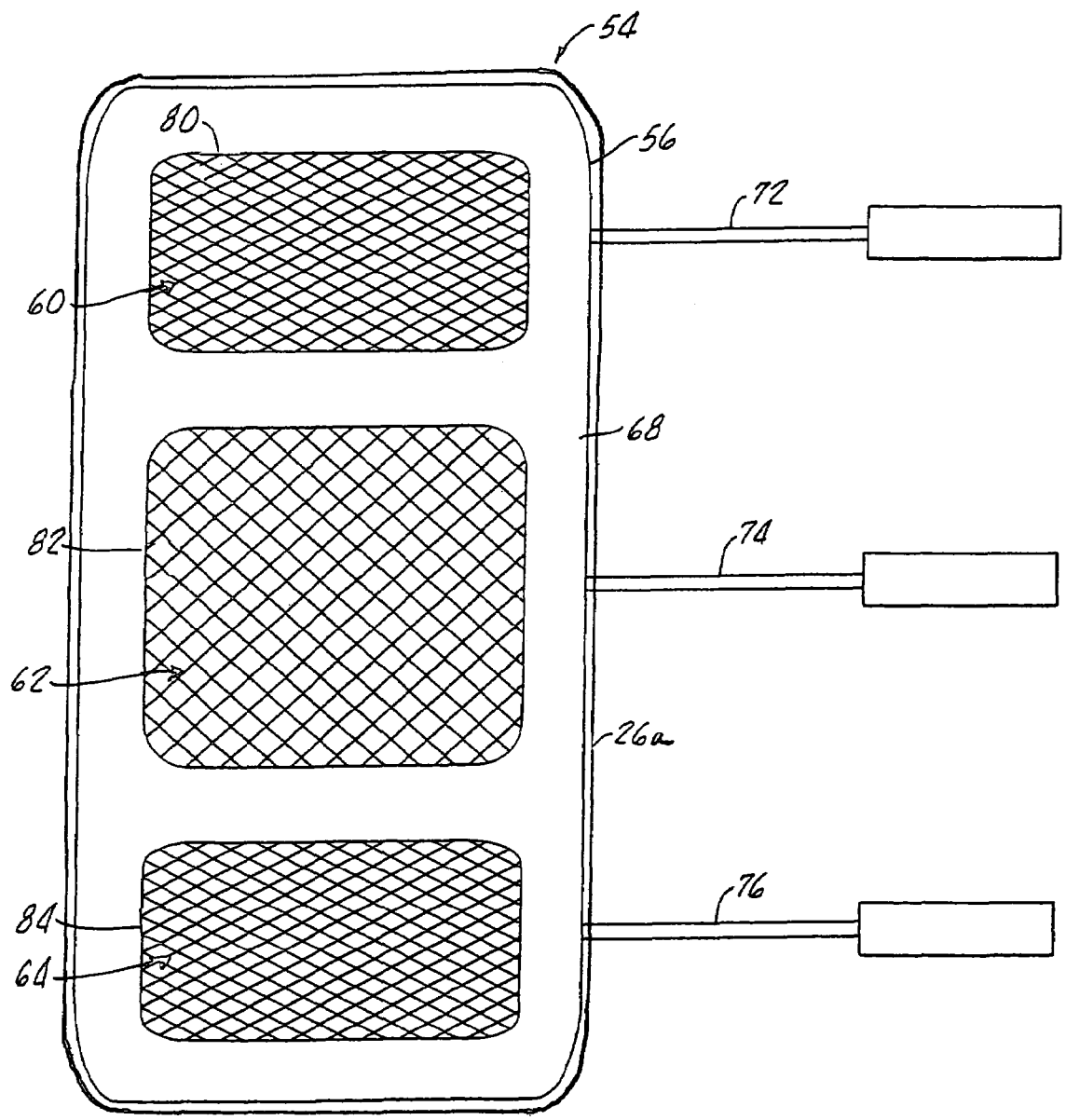
FIG. 3 is a plan view of yet another embodiment of the present invention showing several ink patterns disposed on a single conductive flexible member and a non-conductive flexible sheet extending beyond a perimeter of the member.

With reference to FIGS. 1 and 2, there is shown, in exploded cross-section, a medical electrode 10 in accordance with the present invention, which generally includes a moderately conductive flexible member 12 having a top side 14 and a bottom side 16.

A connector 20, which may include a lead wire 22 and jack 24 is provided with the lead wire 22 in contact with the member top side 14.

A non-conductive flexible oversize sheet 26 covers the conductive flexible member 12 along with the connector 20 in order to prevent inadvertent contact with the conductive member 12 and connector 20. The sheet 26 may be adhered to the flexible member 12 with any suitable adhesive 28 and also holds the lead wire 22 in contact with the member 12. The sheet 26 has dimensions greater than overall dimensions of the member 12 resulting in an edge, or perimeter, 26a which overlaps the member 12, see also FIG. 3. This structure eliminates the need for alignment of the sheet 26 with the member along their peripheries. The adhesive 28 covers the entire sheet 26 include the edge 26a. This enables the electrode 10 to be sealed along the perimeter 26a to a user's skin (not shown). This, in turn, enables bathing or showering by the user without degradation of the electrode/skin coupling. Water is prevented from entering the electrode 10 under the sheet 26.

The lead wire 22 may be of any inexpensive suitable conductive material.

The sheet 12 may be formed from any suitable carbon loaded elastomeric film having suitable surface resistivity of between about $10^2$ ohm/square and about $10^6$ ohm/square, for example, about 5000 ohm/square and a transverse resistivity of between about $10^3$ and about $10^5$ ohm/square, for example, about $10^4$ ohm/square. Suitable polycarbonate polyolefin and a conductive ink pattern 30 may be printed, or otherwise transferred to the conductive member bottom side 16 with various patterns 32, 34 for embodiments 36, 38, as shown in FIGS. 2a and 2b. The ink pattern may have a resistivity of between about 0.1 and about 10 ohm/cm.

With reference again to FIG. 1, the conductive ink pattern 30 contacts a conductive hydrogel adhesive 44, which is utilized for adhering the electrode 10 to a patient's skin, not shown. The conductive hydrogel adhesive is formulated with moderately high conductivity for example a volume resistivity between about $10^2$ and about $10^4$ ohm cm, preferably about 400 ohm cm. Suitable gels are described in U.S. Pat. No. 6,038,464.

A plastic, paper, or other suitable carrier 48 along with a release coating 50 may be provided in order to prevent inadvertent and/or premature adhesion of the patients' skin or other object to the hydrogel. The plastic carrier 48 and release coating 50 is removed prior to application of the electrode 10 to the patients' skin.

Shown in FIG. 3 is another electrode embodiment 54 which includes a moderately conductive flexible member 56 having a plurality of highly conductive ink patterns 60, 62, 64 disposed on a bottom side 62 of the conductive member 56. The conductive ink patterns 60, 62 and 64 may be of various shapes and grid patterns in order to customize the electrical conductivity of the electrode 54 beneath the pattern 60, 62, 64. The adhesive, not shown in FIG. 3, is of moderately high conductivity as hereinabove described.

The spaced apart pattern 60, 62 and 64 act as separate electrodes on a sheet 68 and communicate with lead wires 72, 74, 76 respectively, which are attached to a top side (not shown in FIG. 3) of the conductive member 56 as illustrated in FIG. 1 with the description of the electrode embodiment 10.

The advantage of utilizing a common conductive member 56 with spaced apart ink patterns 60, 62, 64 is that this structure provides uniformity of spacing between the independent electrodes. This in effect provides a template to insure proper electrode placement on a patient's skin.

It should be appreciated that, as shown in FIG. 3, the connector 72, 74, 76 are in placed over the ink patterns 60, 62, 64. The lead wires 72, 74, 76 can be placed anywhere between the borders 80, 82, 84 of the ink patterns 60, 62, 64 since the current distribution across the electrode gel 44 is independently controlled as hereinabove noted.

Referring again to FIGS. 2a and 2b, indicia 90, 92, which may or may not be conductive ink, may be printed on borders 96, 98 and do not interfere with the current density of the electrode 10 if no contact is made with the patterns 32, 34. The borders 96, 98 are created when the conductive ink patterns 32, 34 are disposed on the flexible member bottom side 16 at a spaced apart distance from a perimeter 102, 104 of the conductive member 12. That is, a perimeter 106, 108 of the ink patterns 32, 34 is spaced apart from the perimeters 102, 104.

Figure 4:
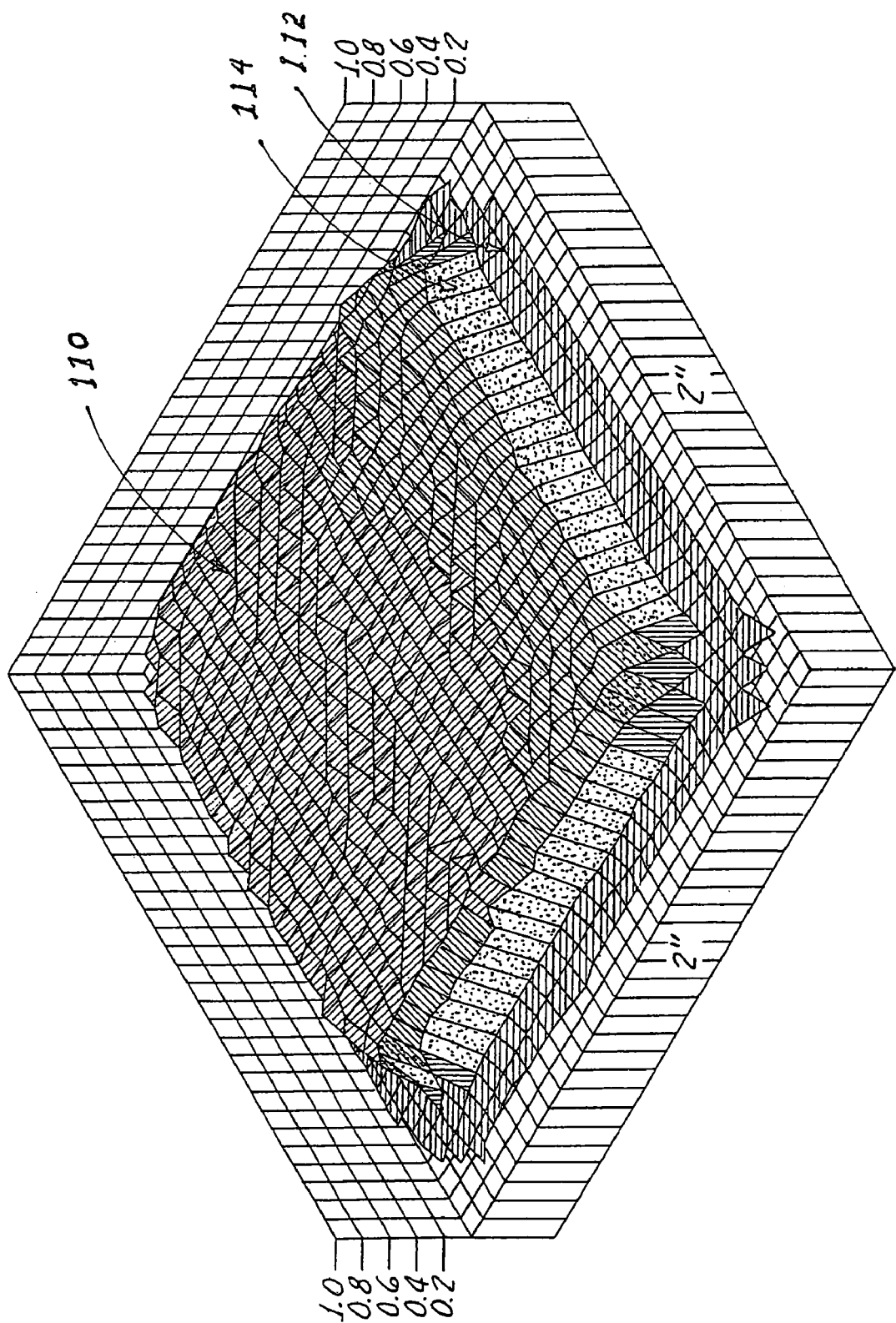
FIG. 4 is a plot of current distribution profile of the electrode shown in FIG. 1, (i.e. an electrode having a moderately conductive flexible member, a highly conductive pattern disposed on the member bottom side and a moderately high conductive adhesive)

FIG. 4 shows the current distribution profile for the electrodes shown in FIG. 2 utilizing a flexible conductive member having a surface resistivity of about 200 ohm/square, a conductive ink pattern having conductivity of about 1 ohm/cm and a hydrogel such as set forth in U.S. Pat. No. 6,038,464 with a volume resistivity of about 400 ohm cm. This patent is incorporated by this reference thereto in its entirety for describing this type of gel in general electrical configuration which may be used to advantage in accordance with the present invention.

As shown in FIG. 4, the conductivity of a 2-inch (50 mm) square electrode is very uniform over almost the entire electrode surface with very little edge effects, i.e. perimeter edges in which non-uniform conductivity occurs, typical with prior art electrodes. In FIG. 4, a center area 110 represents high current density or current transfer by the electrode, the peripheral area 112 represents low or no current density and an intermediate area 114 represents a sharp roll off of current density. Because of the rapid roll off in current density, the efficiency of the electrode is enhanced since most of the electrode is utilized for providing uniform current density without burning edge effects.

Figure 5:
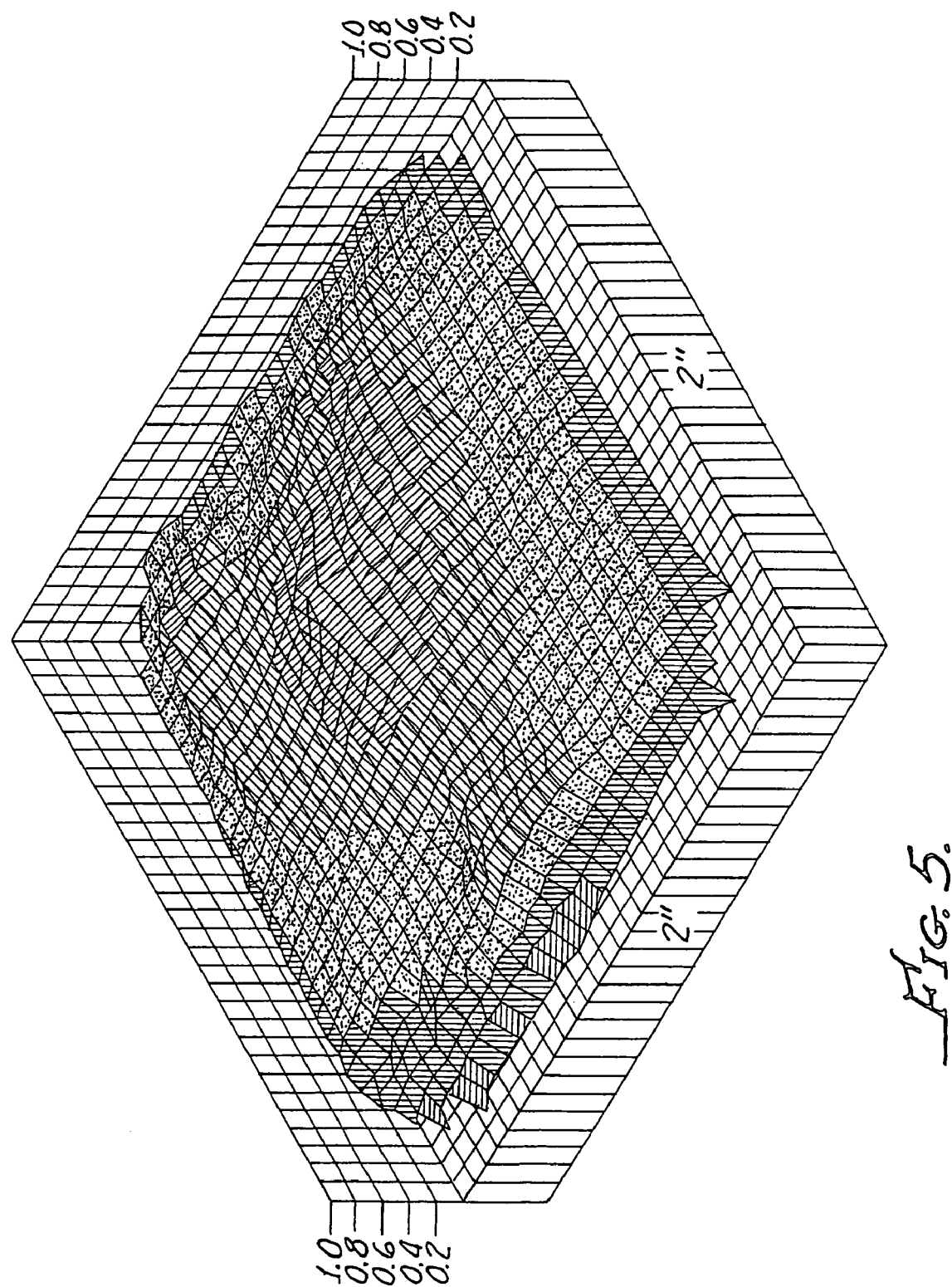
FIG. 5 is a plot similar to FIG. 4, and included for comparison purposes, of the current distribution of an electrode having a moderately conductive flexible member, a highly conductive pattern disposed on the member bottom side and moderately conductive adhesive.

The current density plot of FIG. 4 shows a vastly improved current density over the electrode in FIG. 5 which is identical except for the use of a moderately conductive adhesive (about 1100 ohm cm) instead of a moderately high conductive adhesive (about 400 ohm cm).

It should be clear that the current density shown in FIG. 5 is considerably more non-uniform than the current density shown in FIG. 4. Accordingly, the electrode efficiency in coupling current to a patent (not shown) is severely diminished.

Figure 6:
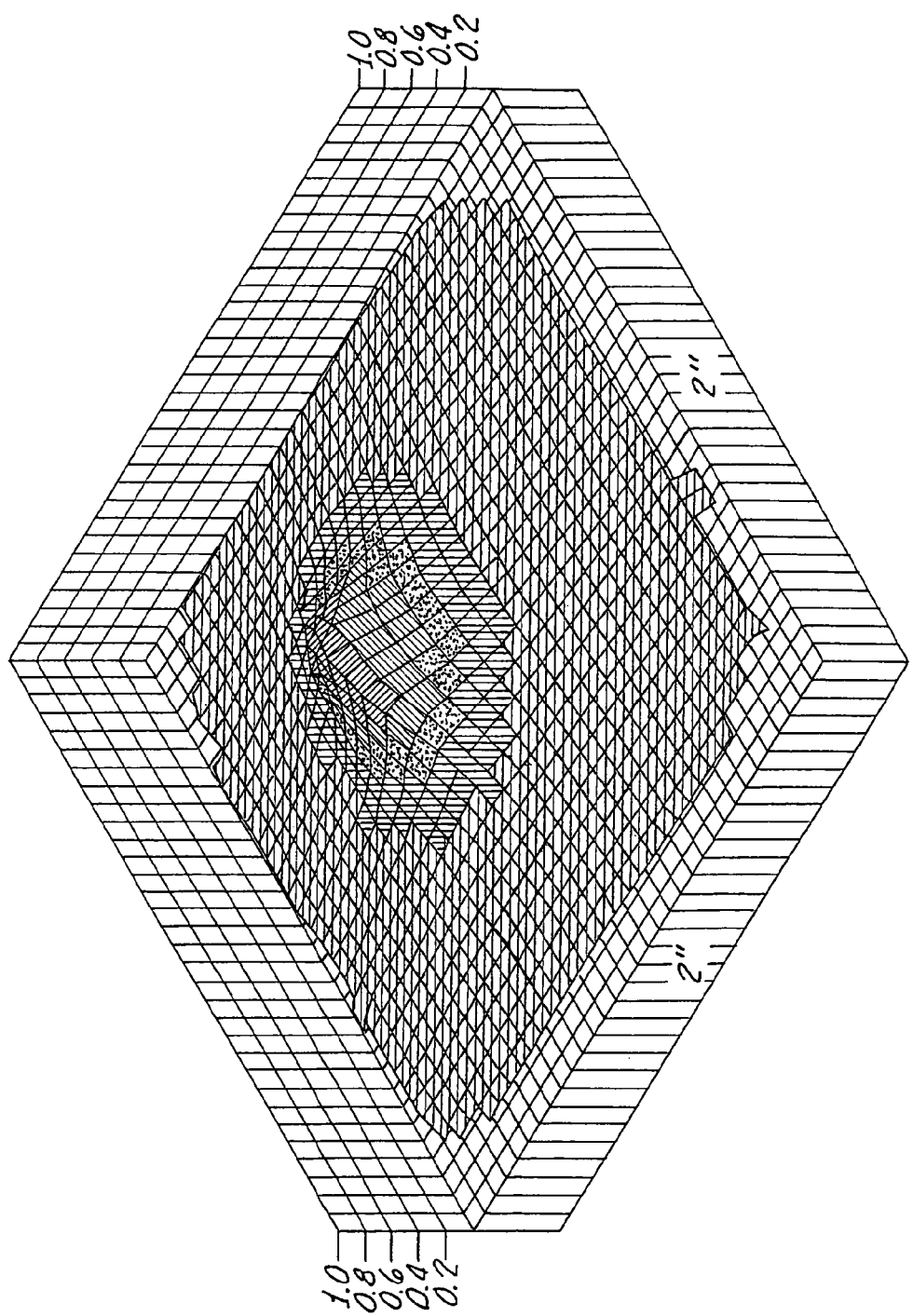
FIG. 6 is a plot similar to FIG. 5, and included for comparison purposes, of the current distribution of an electrode with no highly conductive pattern disposed on a moderately conductive member bottom side, a moderately conductive adhesive and a connector disposed on a top side of the moderately conductive member.

FIG. 6 is a plot of current density of an electrode as constructed similar to the electrode of FIG. 5 with a moderately conductive flexible member and a moderately conductive adhesive but with the lead wire disposed on top of the flexible member and no conductive pattern on the bottom side. The current density shown in FIG. 6 (which is representative of prior art electrodes) is by far inferior to the current densities shown in FIGS. 4 and 5 and illustrates that the unique combination of elements collectively provides an electrode having unexpectedly improved current density.

The difference in conductivity or resistivity between the sheet 12 and the lines 30 as well as the adhesive 44 enables precise control of current distribution which cannot be achieved, for example, with a non-conductive sheet or a highly conductive sheet. The conductivity of the adhesive is selected to be moderately high in order to enable the lead wire 20 to be disposed on top of the sheet 12 instead of in contact with the pattern as with prior art electrode. This effect of adhesive conductivity was heretofore not known and is an unexpected result. In addition, the ink pattern may be of varied conductivity in order to tailor the current through the conductive sheet which may have a thickness of up to about 10 mils, for example, about 1 mil.

Although there has been hereinabove described a specific reverse current-controlling electrode in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A medical electrode comprising:
   a conductive flexible member having a top side and a bottom side;
   a non-conductive flexible sheet disposed over the connector on the conductive flexible member top side, said non-conductive flexible sheet having dimensions greater than said conductive flexible member causing an overlap thereof by a sheet perimeter;
   an adhesive for bonding said non-conductive flexible sheet to the top side of said conductive flexible member and securing said connector to said conductive flexible member top side, said adhesive covering an entire surface of said non-conductive flexible sheet enabling sealing to a user's skin outside of a perimeter of said conductive flexible member;
   a conductive pattern disposed on the conductive flexible member bottom side, the pattern being conterminous within a periphery thereof;
   a conductive adhesive disposed on the conductive flexible member bottom side and covering said conductive pattern, for adhering the electrode to a patient's skin; and
   a current distribution enabling connection in contact with the conductive flexible member topside and over said conductive pattern within borders of the conductive pattern for control of current distribution and establishing electrical contact with an external apparatus.

2. The electrode according to claim 1, wherein said conductive pattern is disposed on the conductive flexible member bottom side at a spaced apart distance from a perimeter of said conductive flexible member to establish a border between a perimeter of said conductive pattern and the conductive flexible member perimeter for providing controlled roll off of electrical current distribution of the electrode.

3. The electrode according to claim 1 wherein said adhesive is disposed over the entire flexible sheet including the sheet perimeter, the adhesive in the sheet perimeter enabling sealing of the electrode to a user's skin.

4. A medical electrode comprising:
a conductive flexible member having a top side and a bottom side;
a plurality of connectors in contact with the conductive flexible member top side, for establishing electrical contact with an external apparatus;
a non-conductive flexible sheet disposed over the connector on the conductive flexible member top side, said non-conductive flexible sheet having dimensions greater than said conductive flexible member causing an overlap thereof by a sheet perimeter;
an adhesive for bonding said non-conductive flexible sheet to the top side of said conductive flexible member and securing said connector to said conductive flexible member top side, said adhesive covering an entire surface of said non-conductive flexible sheet enabling sealing to a user's skin outside of a perimeter of said conductive flexible member;
a plurality of conductive patterns disposed on the conductive flexible member bottom side, the pattern being conterminous within peripheral thereof;
a conductive adhesive disposed on the conductive flexible member bottom side and covering said conductive patterns, for adhering the electrode to a patient's skin; and
a plurality of current distribution enabling connection in contact with the conductive flexible member topside and within border of each of the conductive pattern for control of current distribution and establishing electrical contact with an external apparatus.

5. The electrode according to claim 4, wherein each of said conductive patterns are disposed on the conductive flexible member bottom side at a spaced apart distance from a perimeter of said conductive flexible member to establish a border between a perimeter of each of said conductive patterns and the conductive flexible member perimeter for providing controlled roll off of electrical distribution of the electrode.

6. The electrode according to claim 4, wherein said adhesive is disposed over the entire flexible sheet including the sheet perimeter, the adhesive in the sheet perimeter enabling sealing of the electrode to a user's skin.

* * * * *